Figure 1:
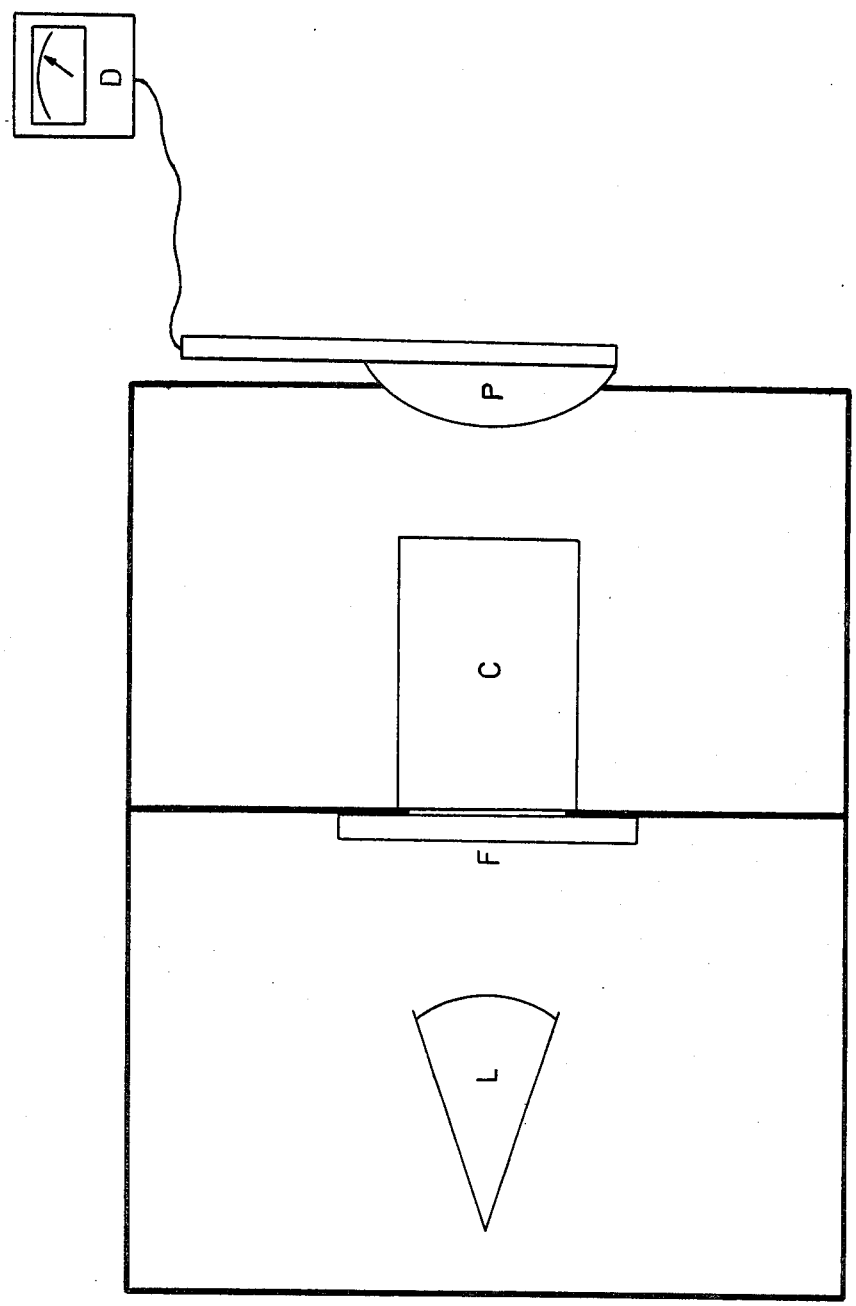

United States Patent [19]

Goldstein

[11] Patent Number: 4,473,651
[45] Date of Patent: Sep. 25, 1984

[54] METHOD FOR THE DETERMINATION OF LECITHIN IN CRUDE OIL

[75] Inventor: Shimon Goldstein, Haifa, Israel
[73] Assignee: Koor Foods Ltd., Haifa, Israel
[21] Appl. No.: 392,213
[22] Filed: Jun. 25, 1982
[30] Foreign Application Priority Data
  Aug. 13, 1981 [IL] Israel .................................... 63568
[51] Int. Cl.$^3$ ...................... G01N 33/28; G01N 21/00
[52] U.S. Cl. ........................................ 436/60; 356/70; 436/71; 436/104; 436/164
[58] Field of Search ...................... 356/36, 70; 436/71, 436/104, 164, 60, 20

[56] References Cited

U.S. PATENT DOCUMENTS 4,257,771  3/1981  Yee .................................. 436/104 X

FOREIGN PATENT DOCUMENTS 358654  11/1972  U.S.S.R. .............................. 436/71

Primary Examiner—Arnold Turk
Attorney, Agent, or Firm—John S. Roberts, Jr.

[57] ABSTRACT

Method for the determination of lecithin concentration in crude oil. A sample of crude oil is admixed with a polar organic sample which does not dissolve lecithin, thus obtaining a suspension. The concentration of lecithin in the suspension is determined by the turbidimetric analysis, by measuring the transmitted light passed through the suspension. According to a preferred embodiment, a tungsten lamp provides the light to be transmitted through the suspension, the light passed being converted to Lux units by Luxmeter and expressed into concentration values of lecithin.

10 Claims, 1 Drawing Figure

METHOD FOR THE DETERMINATION OF LECITHIN IN CRUDE OIL

The present invention relates to a method for the determination of phosphatides. More particularly the invention relates to a method for the determination of lecithin concentration in crude oil and preferably after the degumming operation.

As known phosphatides are complex mixtures consisting of polyhydric alcohols esterified with fatty acids and phosphoric acids, the latter being combined with a nitrogen-containing compound. Phosphatides are present in crude soya beans oil, being extracted from soya beans. Lecithin is a member of phosphatides (also denominated as phospholipids) and containing both water-soluble and fat-soluble groups, will be most useful as emulsifier agent. In the degumming operation, the natural oil is treated with a small amount of water followed by a centrifugal separation. In this manner the lecithin, is recovered and the oil is degummed. After degumming the oil may still contain about 1% by weight of lecithin, its removal being most desirable, generally after removing its content being between 0.2–0.4% (by wt.).

Problems were encountered for a simple and rapid determination of the residual lecithin in the crude oil. The known method is to determine the phosphorus and accordingly the equivalent phosphatide content, by ashing the sample in the presence of zinc oxide followed by colorimetric measurement of phosphorus as blue molybdnum. The method is applicable to crude, degummed and refined vegetable oils. One of the disadvantages of the method, is the long time required in the known procedure, utilizing a large number of reagents and steps which involve charring, heating, cooling, titration etc. The phosphorus is finally determined by a spectrophotometer, measuring the transmittance at 650 m$\mu$, the value obtained being compared with standard working solutions prepared from potassium dihydrogen phosphate in distilled water.

Thus, it would appear that there is a long felt need for a new method for determining the lecithin content in crude oil. It is an object of the present invention to provide an easy method for the determination of lecithin in crude oil. It is another object of the present invention to provide a method for a rapid determination of lecithin in crude oil. Thus the invention consists of a method for a rapid, determination of lecithin concentration in crude oil, wherein the sample of crude oil is admixed with a polar organic solvent which does not dissolve lecithin, the concentration of the lecithin in the resulting suspension being determined by the turbidimetric method wherein the transmitted light passed through said suspension is measured. The simplest method for measuring the light, is by a photometric device wherein the lux units expressed in lumen per square meter are directly determined by a Luxmeter. Subsequently, based on graphs determined with standard solutions of lecithin, the lux units are converted in concentrations units of lecithin.

Polar organic solvents suitable for the method according to the present invention are: acetone, isopropyl alcohol, methyl acetate, binary or tertiary mixtures of acetone with hexanes, methylene chloride, chloroform, benzene, etc.

In order to obtain an efficient light measurement, it is suggested to utilize a light source which provides a high-intensity radiation at a short wave-lengths. A mercury arc or a laser with appropriate filter combination for isolating one of its emission lines, is undoubtely the most convenient source. However, if only a particle count or a determination of the concentration of a particular material is desired, a simple light source such as a tungsten lamp will be most adequate. Generally, in this case the intercalation of an optical filter sill be preferred to block the undesired wavelengths of light around the transmittance at 650 m$\mu$ in order to eliminate the effect of the light transmission on the turbidity determination. Since the intensity of transmitted light is rather small for an accurate determination, a photoelectric cell is desirable to be incorporated after the filter, its purpose being to intercept any light which passes therethrough. Once the intensity of the transmitted light passed through the sample has been determined, the results of lecithin concentration would be evaluated from calibration curves obtained with standard solutions for the respective ranges.

The method according to the present invention is applicable to crude oil and most preferably to crude oil after degumming. It was found that when using crude oil before degumming, some emulsion might be encountered during the mixing with the polar organic solvent which may cause further difficulties in the determination of the lecithin. However, after the degumming operation, wherein the foreign matter causing the emulsion is removed, no problems whatsoever will be encountered, the method being smoothly applied for all types of oils such as corn, soya, sunflower, safflower etc.

The method can be theoretically applied for the determination of lecithin in a broad range of concentrations, but the most accurate results were obtained wherein the concentration was in the range of 0.1–1% by weight. Thus for a sample wherein the lecithin content will be above 1% by weight, a corresponding dilution might be required in order to obtain a most accurate determination.

In the attached FIG. 1 a schematic arrangement of the equipment required for the method according to the present invention is presented. Thus beams of light coming out from a light source L, pass through a filter F, wherein the light transmission is retained in order not to affect the turbidity and further pass through a glass optical cell (C) containing the oil sample in which the lecithin has to be determined. As will be realized the emergent intensity light will be less than the entering intensity light, due to the blockage of some light by the medium with the suspended particles. A photoelectric cell P located after the glass optical cell C, will read the intensity which is converted in Lux units on the Luxmeter D.

While the invention will now be described by two illustrative examples in connection with certain preferred embodiments, it will be understood that it is not intended to limit the invention to these particular embodiments. On the contrary, it is intended to cover all alternatives, modifications and equivalents as may be included within the scope of the invention as defined by the appended claims. Thus, the illustrated FIG. 1 as well as the Examples given which include preferred embodiments will serve only for a better understanding of the practice of this invention, it being understood that the particulars described or sizes of cells used are by way of example and for purposes of illustrative discussion of preferred embodiment of the present invention and are presented to provide what is believed to be the most useful and readily description of procedure as well as of the principles and conceptual aspects of the invention. For example, instead of measuring the light by a Luxmeter, one can envisage to obtain said measurement by an electric instrument such as micro-amperemeter. Based on the same approach, it would be possible to use a digital instrument, wherein the reading will be expressed directly in concentration units of lecithin.

EXAMPLE 1

In a first stage calibration curves were determined based on standardized soya lecithin solutions. These solutions were prepared by dissolving 16.13 g of standard soya lecithin (which contained 62% of phosphatides as acetone insoluble) in 83.87 g of refined soyabean oil to make 100 g of solution. Amounts of 2, 4, 6, 8 and 10 mls of said standardized soya lecithin solution were introduced in a series of volumetric flasks and make up to 100 mls. using refined soybean oil. From each flask an amount of 5 g oil (weighed within 0.01 g accuracy) was introduced in a beaker and mixed with 50 mls acetone. The solution was transferred into a glass optical cell of 1 inch thickness. A blank solution only with acetone alone was also prepared and the absorbance expressed in lux units was measured in each solution accordingly and the reading with the lecithin was obtained. By comparing with the standard solutions a concentration-absorbance graph was prepared in the range of 0.1-1% (wt) lecithin and 300-110 Lux units.

The determination of lecithin was carried out as follows:

A sample of 5 g (weighed within 0.01 g accuracy) soybean oil of an unknown lecithin content, was introduced in a beaker and admixed with 50 mls of acetone. The suspension was transferred into a glass optical cell of one inch thickness. The light absorbance measured by a Luxmeter was 270 Lux units which on the calibration curve appears to correspond to 0.2% (by weight) lecithin content.

EXAMPLE 2

In a similar manner as in Example 1, an amount of 5 g (weighed within 0.01 g accuracy) of soybean oil sample was utilized. The light absorbance measured by a Luxmeter was 210 Lux units, which on the calibration curve appears to correspond to 0.5% (by weight) lecithin content.

I claim:

1. A method for a rapid determination of lecithin concentration in crude oil, comprising mixing a sample of crude oil with a polar organic solvent which does not dissolve lecithin, and determining the concentration of the lecithin in the resulting suspension by turbidimetric analysis wherein transmitted light passed through said suspension is measured.

2. A method according to claim 1, wherein said polar organic solvent is selected from the group consisting of acetone, isopropyl alcohol, methyl acetate, and binary or tertiary mixtures of acetone with hexanes, methylene chloride, chloroform or benzene.

3. A method according to claim 1, wherein the crude oil utilized is of the type obtained after a degumming operation.

4. A method according to claim 1, wherein the lecithin to be determined in the crude oil, is in the range of 0.1%-1% by weight.

5. A method according to claim 1, wherein the transmitted light is obtained by utilizing a source which provides a light-intensity radiation.

6. A method according to claim 5, wherein the source of light is a tungsten lamp.

7. A method according to claim 6, wherein an optical filter is utilized in order to block undesired wavelengths of light around 650 m$\mu$.

8. A method according to claim 1, wherein a photoelectric cell is located after the sample to measure the intensity of transmitted light.

9. A method according to claim 8, wherein the light passed through the sample is converted to Lux units by a Luxmeter.

10. A method according to claim 9, wherein the reading of the Luxmeter is interpreted into concentration values by comparing with graphs of standard solutions of lecithin.

* * * * *